United States Patent
Evenstad et al.

(10) Patent No.: US 9,880,097 B2
(45) Date of Patent: Jan. 30, 2018

(54) APPARATUS AND SYSTEM FOR SIMULTANEOUSLY MEASURING PARTICLE CONCENTRATION AND BIOCONTAMINANTS IN AN AEROSOL PARTICLE FLOW

(71) Applicant: TSI, Incorporated, St. Paul, MN (US)

(72) Inventors: Jim Evenstad, Mahtomedi, MN (US); Dahu Qi, Woodbury, MN (US); Peter P. Hairston, North Oaks, MN (US); Darrick Niccum, Vadnais Heights, MN (US)

(73) Assignee: TSI Incorporated, Shoreview, MN (US)

( * ) Notice: Subject to any disclaimer, the term of this patent is extended or adjusted under 35 U.S.C. 154(b) by 0 days.

(21) Appl. No.: 14/345,478

(22) PCT Filed: Sep. 18, 2012

(86) PCT No.: PCT/US2012/055917
§ 371 (c)(1),
(2) Date: Mar. 18, 2014

(87) PCT Pub. No.: WO2013/043600
PCT Pub. Date: Mar. 28, 2013

(65) Prior Publication Data
US 2014/0354976 A1 Dec. 4, 2014

Related U.S. Application Data

(60) Provisional application No. 61/536,875, filed on Sep. 20, 2011.

(51) Int. Cl.
*G01N 21/53* (2006.01)
*G01N 21/27* (2006.01)
(Continued)

(52) U.S. Cl.
CPC .......... *G01N 21/53* (2013.01); *G01N 1/2211* (2013.01); *G01N 15/1459* (2013.01);
(Continued)

(58) Field of Classification Search
CPC .......... G01N 21/53; G01N 2001/2223; G01N 21/65; G01N 2015/0046; G01N 15/1459; G01N 1/2211
See application file for complete search history.

(56) References Cited

U.S. PATENT DOCUMENTS

| 4,301,002 A | 11/1981 | Loo |
| 4,710,025 A | 12/1987 | Wyatt et al. |

(Continued)

FOREIGN PATENT DOCUMENTS

| DE | 100 30 134 A1 | 1/2002 |
| WO | 2009/064868 | 5/2009 |

OTHER PUBLICATIONS

Extended European Search Report, EP Application No. 12833801.8-1554, dated Jun. 15, 2015.

(Continued)

*Primary Examiner* — Michael A Lyons
*Assistant Examiner* — Violeta A Prieto
(74) *Attorney, Agent, or Firm* — Kagan Binder, PLLC (57) ABSTRACT

An apparatus and method for improving aerosol particle characterization and detection accuracy in clean room applications that includes an optical particle sizer that receives a particle containing aerosol sample at a higher flow rate which is operatively coupled to an inertial aerosol concentrator for concentrating particles received from the optical particle sizer and delivering a lower flow rate, particle enriched output. The system further includes an optical sensor for sensing of intrinsic particle fluorescence of the lower, particle-enriched flow, since intrinsic fluorescence is
(Continued) a useful indicator of biological particles and biological particle viability, including bacterial particles. The system as a whole provides a measure derived from a single inlet flow both of total particles and of viable microbial particles based on their spectroscopic properties.

27 Claims, 8 Drawing Sheets (51) Int. Cl.
*G01N 21/64* (2006.01)
*G01N 21/65* (2006.01)
*G01N 21/94* (2006.01)
*G01N 1/22* (2006.01)
*G01N 15/14* (2006.01)
*G01N 21/3504* (2014.01)
G01N 21/35 (2014.01)
G01N 21/67 (2006.01)
G01N 21/71 (2006.01)
G01N 15/00 (2006.01)

(52) U.S. Cl.
CPC ......... *G01N 21/27* (2013.01); *G01N 21/3504* (2013.01); *G01N 21/64* (2013.01); *G01N 21/6486* (2013.01); *G01N 21/65* (2013.01); *G01N 21/94* (2013.01); G01N 21/35 (2013.01); G01N 21/67 (2013.01); G01N 21/718 (2013.01); G01N 2001/2223 (2013.01); G01N 2015/0046 (2013.01)

(56) References Cited

U.S. PATENT DOCUMENTS

| | | | |
|---|---|---|---|
| 5,118,959 A | 6/1992 | Caldow et al. | |
| 5,701,012 A | 12/1997 | Ho | |
| 5,895,922 A | 4/1999 | Ho | |
| 6,230,572 B1 | 5/2001 | Pui et al. | |
| 6,594,001 B1 | 7/2003 | Yabusaki | |
| 6,831,279 B2 | 12/2004 | Ho | |
| 7,261,007 B2 | 8/2007 | Haglund et al. | |
| 7,407,531 B2 | 8/2008 | Flagan et al. | |
| 7,869,037 B2 | 1/2011 | Kurozumi et al. | |
| 2003/0098422 A1 | 5/2003 | Silcott et al. | |
| 2004/0010379 A1 | 1/2004 | Craig et al. | |
| 2004/0080747 A1 | 4/2004 | Cerni et al. | |
| 2006/0054017 A1* | 3/2006 | Haglund et al. | 95/32 |
| 2010/0186524 A1* | 7/2010 | Ariessohn et al. | 73/863.22 |

OTHER PUBLICATIONS

Hairston et al., "Design of an Instrument for Real-time Detection of Bioaerosols Using Simultaneous Measurement of Particle Aerodymanic Size and Intrinsic Fluorescence," Journal of Aerosol Science, vol. 28, No. 3, Jan. 1, 1997, pp. 471-482.
Kotaro et al., "Development of a novel real-time pollen-sorting counter using species-specific pollen autofluorescence," Aerbiologia, vol. 26, No. 2, Dec. 12 2009, pp. 99-111.
Pan et al., "Bio-Aerosol Fluoresence Detecting and characterising bio-aerosols via UV light-induced fluorescence spectroscopy", Optics of Biological Particles, vol. 238 of the series NATO Science Series, pp. 63-164 (2007).
Maintenance Schedule from Manual for TSI Model 3314 UV-APS Spectrometer (3 pages) (circa 2003).
Aerotrak® Portable Particle Counter Models 9310 & 9510 Spec Sheet, © 2017 TSI Incorporated, retrieved from http://tsi.com/uploadedFiles/_Site_Root/Products/Literature/Spec_Sheets/AeroTrak_Portable_9310-9510_5001207-Web-A4.pdf (2 pages).
BioLaz® Real-Time Microbial Monitor Spec Sheet, © 2014 Particle Measuring Systems, Inc., available from http://www.pmeasuring.com/en/products/microbial/biolaz-real-time-microbial-monitor (2 pages).
"Guidance for Industry, Sterile Drug Products Produced by Aseptic Processing—Current Good Manufacturing Practice", U.S. Department of Health and Human Services, Food and Drug Administration, Sep. 2004 (63 pages).
Comparison of IMD-A® 300 and 350 Models, Technical Bulletin, Azbil BioVigilant, Inc., Mar. 4, 2013 (7 pages).
"Fundamentals of an Environmental Monitoring Program", Technical Report No. 13 (Revised), © 2014 Parenteral Drug Association, Inc., pp. 1, 8, 9, and 17.
IsoAir® 310P Aerosol Particle Sensor Spec Sheet, © 2015 Particle Measuring Systems, Inc., available from http://www.pmeasuring.com/en/products/air-and-condensation/isoair-310p-aerosol-particle-sensor.
"<1116> Microbiological Control and Monitoring of Aseptic Processing Environments", © 2013 USPC Official Dec. 1, 2012-Apr. 30, 2013 General Chapters, retrieved on Jan. 9, 2013 from http://www.uspnf.com/uspnf/pub/getPFDocument?usp=35&nf30&supp=2&collection=/db/ . . . (27 pages).

\* cited by examiner 28.3 l/min INLET FLOW

100

110

PARTICLE COUNTER — 120

PARTICLE CONCEN-TRATOR — 130

HEPA FILTER

VIABILITY DETECTOR — 140

150 — COLLECTION FILTER

→ 27.3 L/min CONCENTRATOR EXHAUST
1.0 L/min CONCENTRATED AEROSOL + 4.0 L/min CLEAN "SHEATH" FLOW
→ 5.0 L/min VIABILITY/FILTER EXHAUST

Typical Particle Transmission Efficiency Versus Particle Size for an Inertial Aerosol Concentrator

300

Concentration Efficiency vs. Particle Size

Midrange Efficiency

50% Efficiency

Percneet Efficiency (%) vs. Particle Size, μm

APPARATUS AND SYSTEM FOR SIMULTANEOUSLY MEASURING PARTICLE CONCENTRATION AND BIOCONTAMINANTS IN AN AEROSOL PARTICLE FLOW

CLAIM OF PRIORITY AND CROSS REFERENCE TO RELATED APPLICATION

The present application claims priority to U.S. Provisional Application No. 61/536,875, filed Sep. 20, 2011, and to PCT/US2012/055917 filed on Sep. 18, 2012 (published as WO 2013/043600 on Mar. 28, 2013), the disclosures of which are hereby incorporated by reference in their entireties.

BACKGROUND OF THE INVENTION

Condensation Particle Counters (CPCs) and Optical Particle Counters (OPCs) are apparatus typically used in various applications to detect and count airborne particles.

Clean areas for manufacturing of pharmaceutical products are required to be monitored for both total particle contamination and microbial contamination. ISO Standard 14644 defines clean room classification standards for total particle concentration versus particle size, while ISO 14698-1 establishes concentration standards for biocontamination control. Real time monitoring, with reporting within minutes, of both total particles and biological particles is highly desirable to provide rapid response and correction of contamination, and to provide a fast report that processed materials are free of contamination. Real time monitoring contrasts with traditional batch monitoring methods in which particles are collected and incubated over multiple hours or days to produce colony counts that can be related to viable bacterial particles. For effective monitoring, inspection of at least one cubic meter of air in one hour or less is very desirable.

SUMMARY OF THE INVENTION

In one example embodiment of the present invention, an apparatus and system for improving aerosol particle characterization and detection accuracy in pharmaceutical and medical device clean room applications is taught herein. In particular, the particle characterization system includes, but is not limited to, a sensor apparatus for sensing of optical particle size in an aerosol sample at a higher flow rate {e.g., 28.3 L/min (1 ft3/min)}, and an inertial aerosol concentrator for generating a higher concentration of particles from the higher flow rate optical particle sizing output flow to a lower flow rate enriched particle concentration fed to a fluorescence sensing subsystem for detecting microbial particles. The subsystem for sensing of intrinsic particle fluorescence of the lower, particle-enriched flow is a useful indicator of biological particles and biological particle viability, including bacterial particles. In a related embodiment, a collection filter is included for capturing particles from the enriched sample aerosol flow.

For optical sizing and particle counting, the lower particle size limit (typically 0.3 μm to 0.5 μm in diameter) is determined by the scattered light signal. It has been discovered that the intrinsic fluorescence of biological particles is significantly weaker that the light scatter signal used for optical sizing, so the inspected flow rate can be higher for optical particle sizing than for intrinsic fluorescence sensing. Further, since inertial concentration is inefficient at smaller particle sizes (e.g., <1-2 μm), this allows the higher flow rate optical particle sizing to include a substantial portion of particles smaller than those particles efficiently transported by the aerosol concentrator. The intrinsic fluorescence sensing covers the size range that is transported efficiently by the inertial concentrator (typical 1 or 2 μm to approximate 10 μm), which covers the size range of most biological aerosol particles.

In a related embodiment, the optical size of particles are measured in the same optical cell as used for fluorescence sensing. In addition, the transit time from the higher flow particle sizing to the lower flow fluorescence sensing can be predetermined. By using either (a) the optical size measurement at each particle sizing location (the optical sizing and the fluorescence and light scatter location), or (b) the transit time between the optical and fluorescence size location, or (c) both methods (a) and (b), the fraction of all particles in a given optical size range (or size bin) that have fluorescence characteristics of biological particles can be determined.

In another example embodiment, an instrument and method for characterizing aerosols includes means for optically sizing particles in an aerosol flow at an intake flow rate including particles of an aerodynamic size which are too small be inertially concentrated at near atmospheric pressure. Subsequent to optical particle sizing, the next step is supplying the same aerosol flow to an inertial particle concentrator, and then supplying the concentrated aerosol flow, containing primarily particles of a size sufficiently large to be inertially concentrated a near atmospheric pressure, for characterization by a second method, such as fluorescence (also LIBS (Laser Induced Breakdown Spectroscopy), SIBS (Spark Induced Breakdown Spectroscopy), Raman, IR absorption), which are enhanced by a flow rate lower than the intake flow rate to attain sensitivity sufficient to achieve the second characterization. The second level of characterization or differentiation help to discriminate between viable and nonviable particles or microorganisms from nonviable particles. For example, the particles may be excited by one wavelength of light or energy and the emissions from the particles are captured by collecting two bands (or wavelengths) of emission data.

In a related embodiment, a particle characterization system is disclosed that includes an aerosol particle concentrator configured to receive an aerosol sample at a first inlet flow rate and configured to emit a portion of the aerosol sample at a second "major" outlet flow rate that is lower than the first flow rate. The system further includes an optical particle counter configured to receive the particle containing major outlet aerosol sample from the aerosol concentrator and adapted to use light scattering to count the particles in the aerosol sample. The particle characterization further includes a measurement device configured to receive the aerosol sample at a third "minor" flow rate and adapted to spectrally measure light emitted or absorbed by the particles in the aerosol sample. Typically, the concentrator is configured such that the minor outlet flow rate contains most of the particles larger than a cut-point size of approximately 1 to 3 μm and is significantly lower (by a ration 5:1 to 30:1) than the major flow rate, which contains most particles smaller than the cut point size. In a yet another related embodiment, the system includes means for characterizing a particle size-dependent transport efficiency of the aerosol concentrator's particle size-dependent transport efficiency and means for correcting downstream particle count values to reflect an actual concentration of particles entering the particle characterization system.

DETAILED DESCRIPTION OF THE INVENTION

Following below are more detailed descriptions of various related concepts related to, and embodiments of, methods and apparatus according to the present disclosure for an improved system and method for characterizing particles in an aerosol flow for pharmaceutical and clean room (such as for medical device or semiconductor) manufacturing. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

The various embodiments described herein are particularly applicable for monitoring clean areas, such as for pharmaceutical and medical device manufacturing, in which it is desirable or mandated by industry standards to monitor the air quality for both (a) total particle counts in each of selected size ranges, and (b) biological particle count. The various embodiments are especially advantageous where a relatively large volume of air (e.g., 1 m3) is desired to be inspected in a moderate time period (e.g., less than 1 hour). For biological sensing based on fluorescence, typical inspected flow rates that can be achieved are on the order of 1 to 5 L/min, which at 5 L/min would require 200 minutes to inspect 1 m3 without particle concentration.

Figure 1:
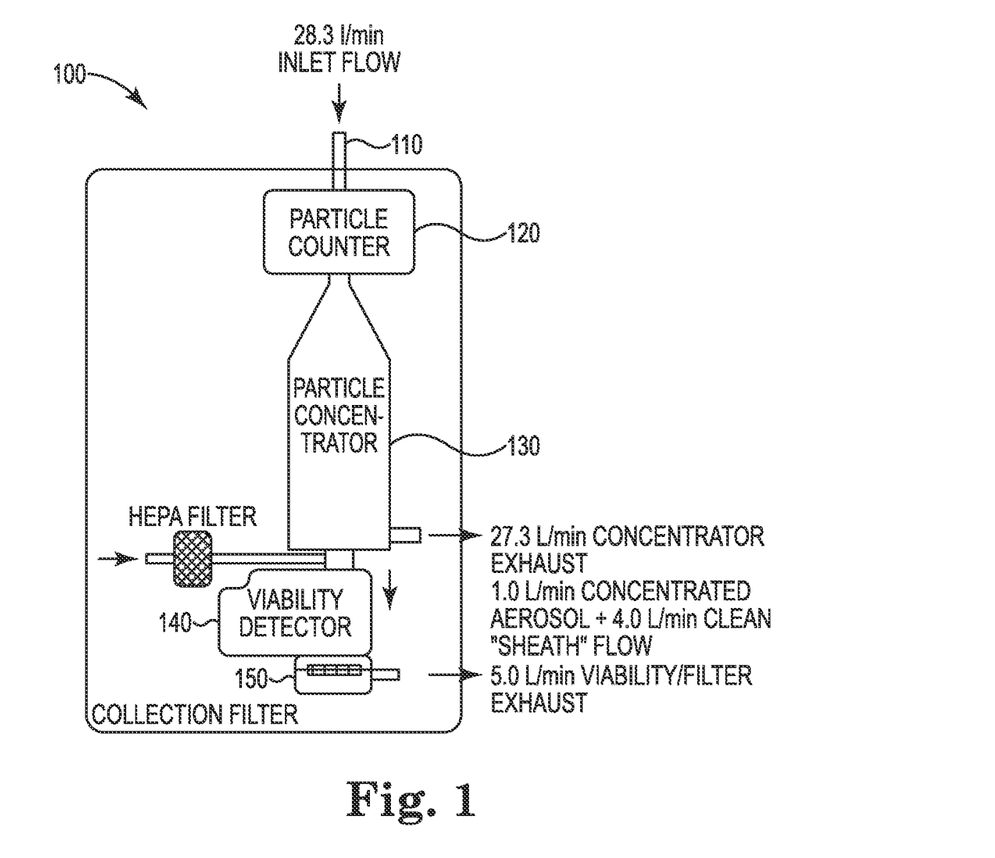
FIG. 1 is a schematic of a biological optical particle characterization system according to the teachings of the invention.
Figure 2:
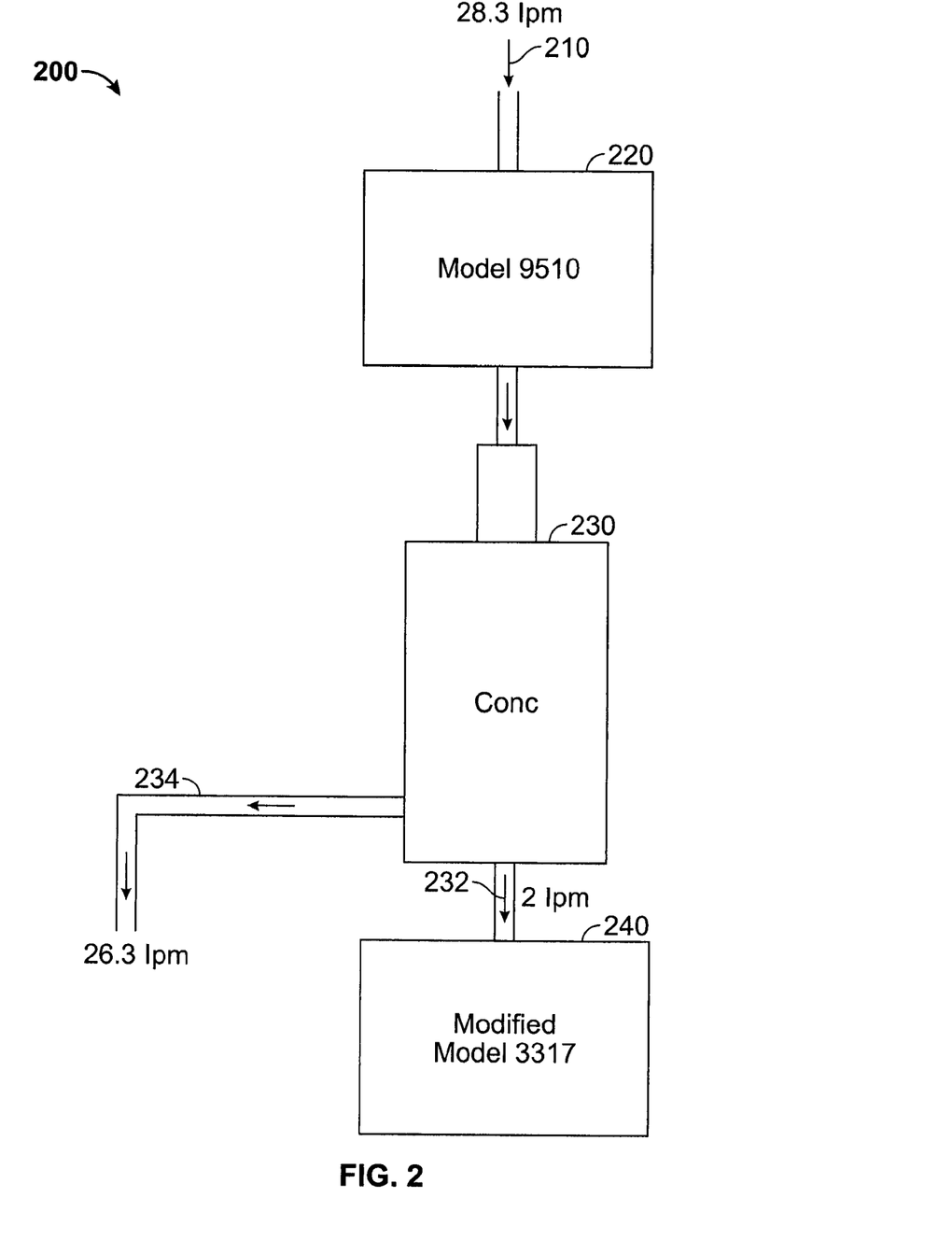
FIG. 2 is another embodiment of a biological optical particle characterization system according to the teachings of the invention.
Figure 3:
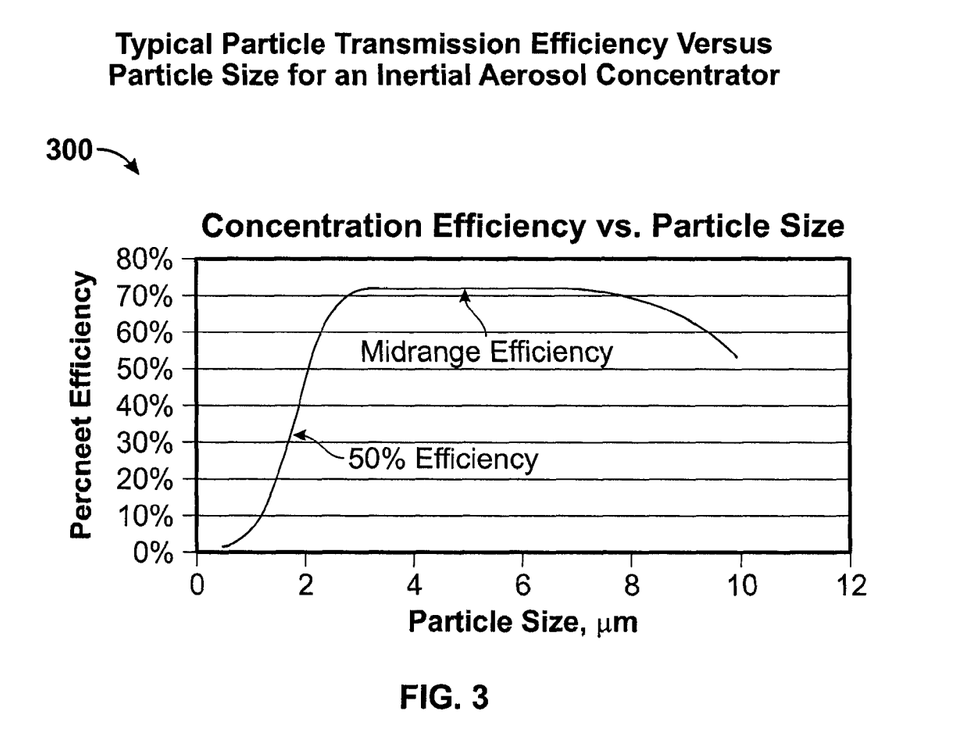
FIG. 3 is a graph illustrating particle transmission in an inertial aerosol concentrator.

Referring now to FIGS. 1-3, an example embodiment of a biological optical particle characterization/detection/counter system 100 provides real time contamination monitoring in an industrial environment, including but not limited to, pharmaceutical processing clean areas. In this example embodiment, characterization system 100 incorporates in a single instrument three key functions for clean area particle characterization/counting and monitoring: a particle sizer or counter 120 configured for particle sizing to count, size, and record in real time of all particles larger than 0.5 micrometers (μm) sorted into, for example, 6 size ranges based on measurement of individual particle light scattering (sorting refers to accumulating the number of particles into the respective size ranges for reporting). In this example, particle counter 120, of detection system 100, receives an aerosol sample at its inlet 110 at a high flow rate (about 28.3 liters per minute (lpm)). An inertial aerosol concentrator 130 is operatively coupled for its inlet to intake the aerosol flowing through counter 120 and is configured to deliver (or emit) at a slower "minor" flow rate (about 1-4 liters per minute) a portion of the received inlet aerosol sample including mostly of the larger particles in the inlet aerosol sample (those to the right of a concentrator transmission efficiency curve as illustrated in FIG. 3) to a viability particle detector 140 (such as a Laser Induced Fluorescence (LIF) detector). In this example embodiment, the concentrator "major" flow exhaust is at about 27.3 liters per minute with the minor flow passing through detector 140 at a rate of about 1 liter per minute with a clean sheath flow of about 4 liters per minute. It should be noted that system 100 can be generally used to measure, with one inlet flow, total particle counts in selected size ranges and also particles that have a fluorescent property. In this example embodiment, the particle characterization system further includes a means for or a unit for combining a first set of particle measurement data from the optical particle counter and a second set of particle measurement data from the spectral measurement device to generate a total particle measurement or count for the aerosol sample at the first flow rate.

Figure 1A:
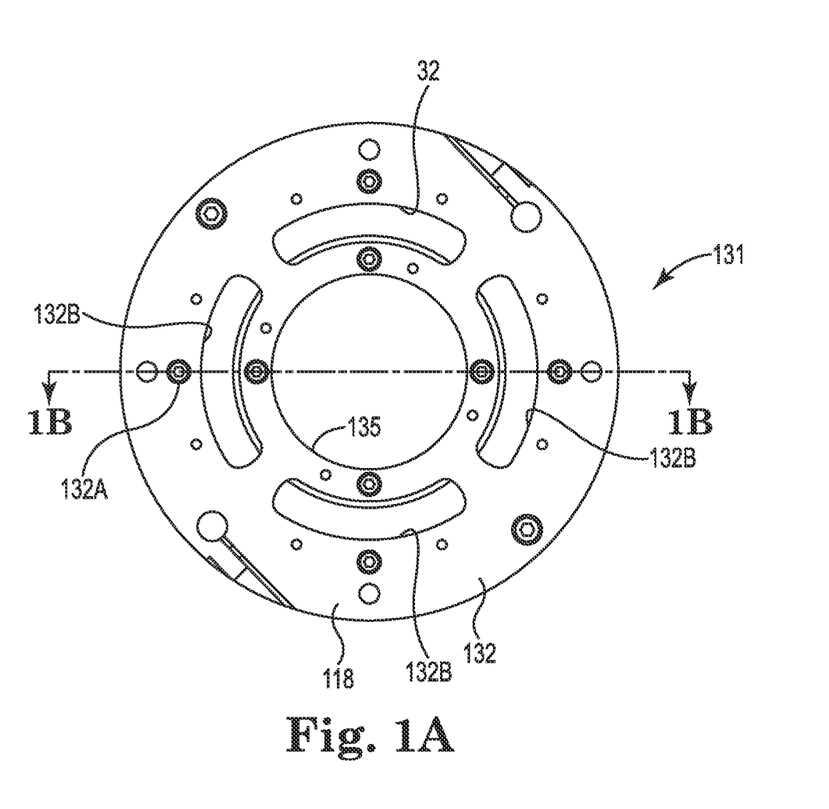
FIG. 1A is a frontal view of an aerosol particle concentrator device according to the teachings of the invention.
Figure 1B:
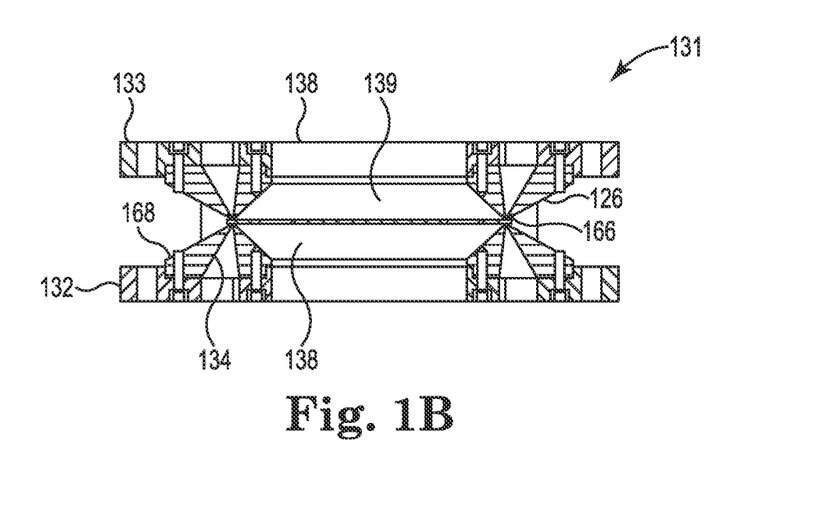
FIG. 1B is a side sectional view of taken along the line 4-4 of FIG. 1A.
Figure 1C:
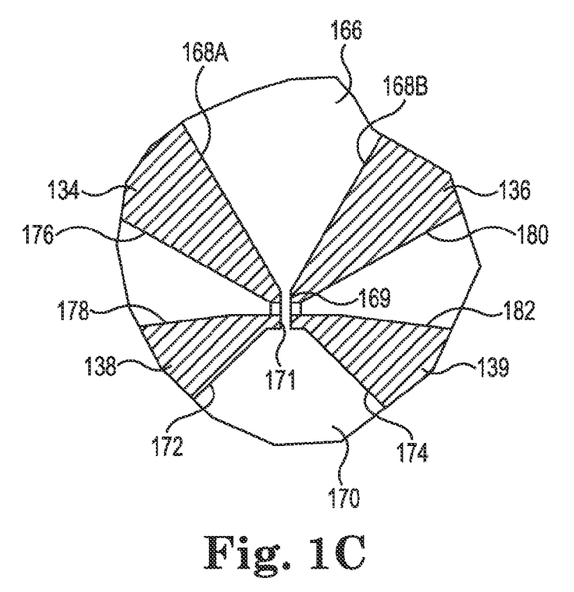
FIG. 1C is an enlarged view showing part of FIG. 1B.
Figure 1D:
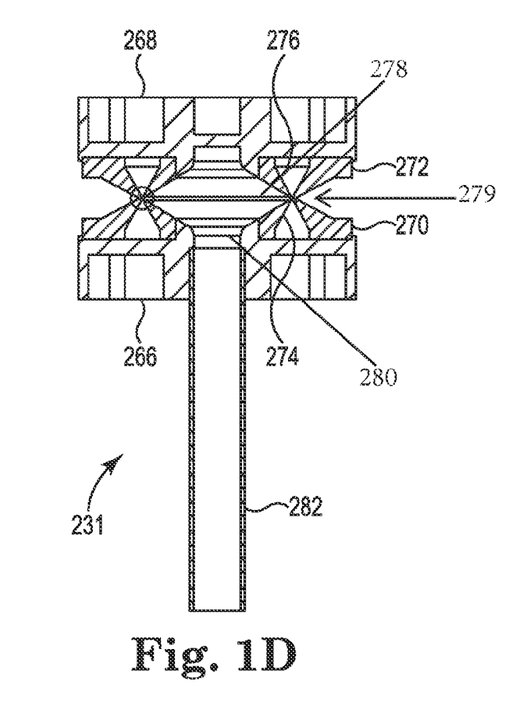
FIG. 1D is a side sectional view of an alternative embodiment of an aerosol particle

Referring now more specifically to particle concentrator 130 of FIG. 1 and to other concentrator embodiments of FIGS. 1A-1D, FIG. 1A illustrates a concentrator assembly 131 while FIG. 1D illustrates another concentrator assembly 231 either of which are located within the particle concentrators of the systems described herein. There is shown in FIGS. 1A and 1B an aerosol particle concentrator assembly 131 that includes a disk shaped housing 118 formed of several annular components. As best seen in FIG. 1A, the annular components include a frontal housing section 132 and a rearward housing section 133. Additional annular components that cooperate to form fluid flow directing nozzles, include an outer nozzle section 134, a nozzle section 136 (seen in FIG. 1C), an inner nozzle section 138, a nozzle section 139 (see in FIG. 1B). Bolts 132A are used to couple the annular components together and maintain them in coaxial alignment.

A plurality of arcuate openings 132B are formed through the frontal wall portion of housing section 132. Rearward housing section 133 includes similar arcuate openings. Also formed through housing section 132 is a circular central opening 135.

Nozzle sections 134 and 136 cooperate to form an annular acceleration nozzle 166 adapted to receive an aerosol and guide the aerosol into housing 118 while accelerating the aerosol. The aerosol is drawn radially inward from a nozzle entrance 168 toward a nozzle exit aperture 169 having opposed annular radial surfaces. Opposed interior surfaces 168A and 168B of nozzle 166 are inclined at an angle of about 30 degrees from the radial direction, to provide a convergence to accelerate the incoming aerosol.

Nozzle sections 138 and 139 cooperate to provide an annular receiver nozzle 170, aligned with and radially spaced apart from acceleration nozzle 166. Sections 138 and 139 are spaced apart transversely, i.e. axially with respect to the housing, to form a receiver nozzle aperture 171 having opposed annular surfaces. Opposed annular inclined surfaces 172 and 174 provide a divergence in the radially inward direction, to decelerate aerosols moving through the nozzle.

Between nozzles 166 and 170, the nozzle sections have respective annular inclined surfaces 176, 178, 180, and 182. Opposed annular surfaces 176 and 178, and opposed surfaces 180 and 182, cooperate to provide diverging passages in opposite directions, axial with respect to housing 118 and perpendicular to the radial direction of aerosol flow through nozzle aperture 169.

A fluid-drawing system including a vacuum pump and several valves, not shown in FIGS. 1A-1C, is used to apply a partial vacuum to receiver nozzle 170 and to the gap between nozzles 166 and 170. This creates a fractionation zone between the nozzles in which the incoming or primary aerosol flow is divided into a secondary flow that travels axially away between surfaces 176 and 178 (and also between surfaces 180 and 182), and a tertiary flow that enters receiver nozzle 170. Various negative pressures are selectively adjusted to provide the secondary flow as a major flow constituting about 90 percent of the primary aerosol flow in terms of volume per unit time, while the tertiary flow constitutes a minor flow at about 10 percent of the primary flow. The separation of larger particles from the secondary flow, and their merger into the tertiary flow to provide a highly concentrated aerosol.

Given the shape of housing 118, the interior of acceleration nozzle 136 forms an endless annular or circumferential slot for receiving the aerosol. In fact, device 131 can be conveniently thought of as a circumferential slot virtual impactor. The design is particularly well suited for uses that demand portability, compactness, and low power consumption. As previously noted, power consumption can be reduced by narrowing the slot width, i.e. the axial width of exit aperture 169. This requires considerable slot length, e.g. one hundred times the slot width, to achieve satisfactory volumetric flow rates. In the circumferential slot design, the slot "length" is substantially equal to the circumference of the housing. A conventional linear slot virtual impactor, to achieve the same flow rate through the same slot width, would need to be over three times as long as the diameter of housing 118. An additional advantage with respect to linear slot designs is that annular slot eliminates the undesirable end effects that negatively influence the performance of linear devices.

The circumferential slot nozzle performs in the same manner as linear slot designs, provided that the total slot length and critical geometries are equivalent, and that the radius of curvature of the slot is much greater than the slot width. Short linear slot impactors may experience increased particle losses due to end effects, which are absent in systems with circumferential slots. In an exemplary circumferential virtual slot device, the diameter of the circumferential slot is 70 mm (2.75"), for a total slot length of 219 mm (8.64 inches). The acceleration nozzle slot width is 0.51 mm (0.020 inches), providing a ratio of the radius of slot curvature to slot width of approximately 69. A sampling flow rate with a low pressure drop requires a long slot. For the exemplary device, the ration of slot length to slot width is 4:32.

FIG. 1D is a sectional view of an alternative embodiment aerosol particle concentration device 231. Annular housing sections 266 and 268 cooperate with annular nozzle sections 270, 272, 274, and 276 as before to provide an annular acceleration nozzle 278, an exit aperture 279, a receiver nozzle 280, and diverging passages between the two nozzles. A conduit 282, attached to the housing at the center of housing section 266, conducts the tertiary aerosol flow away from the device.

In this example embodiment, viability particle detector 140 is configured for detection and to sense and record in real time all viable biological particles based on spectral measurement of individual particle intrinsic fluorescence characteristics. In another related embodiment, the viability measurement is also made with other measurement techniques including but not limited to, LIBS (Laser Induced Breakdown Spectroscopy), SIBS (Spark Induced Breakdown Spectroscopy) and Raman (IR absorption).

In yet another embodiment, characterization system 100 includes a particle collector/filter 150 configured for collection onto a viability preserving gel filter for post-analysis and confirmation of any real time viable particle detection and to preserve samples for biological species identification. In this example embodiment, filter 150 is a 37 mm collection filter. In this example embodiment, the exhaust from system 100 is at about 5 liters per minute exiting the viability filter 150.

In a related embodiment, particle/filter collector 150 of system 100 receives the 1.0 L/min aerosol that has passed through viability detector 140 and collects particles on a gelatin membrane filter (for example, Sartorius ALK-GELATIN-FILTER). The flow through the particle collector also includes 4.0 L/min HEPA filtered clean "sheath air" that surrounds and directs the 1.0 L/min sample aerosol to flow smoothly through the viability detector. The gel membrane filter retains >99.9% of bacterial particles and supports their viability for more than 8 hours in laboratory settings. This filter is easily removed for conventional incubation or other analysis methods for species identification of any bacteria detected.

Referring now to FIG. 2, in this embodiment, system 200 provides a fully integrated monitoring solution for clean room environments. FIG. 200 describes an embodiment of the system in which the system of FIG. 100 is implemented using components of existing particle characterization instruments. In this example embodiment, particle sizing and counting in the optical particle counter incorporates the functional components of a Model 9510 "Aerotrak™" Particle Counter (manufactured by TSI, Inc. of Shoreview, Minn.) that has been qualified for clean room monitoring under ISO 14644-1, and ISO 21501-4. The 9510 AeroTrak counts particles using light scattering technology, in which particles pass through a 660 nm laser diode beam and the intensity of light scattered is measured, and reports particle concentration in one of six size bins: 0.5-0.7 µm, 0.7-1.0 µm, 1.0-3.0 µm, 3.0-5.0 µm, 5.0-10.0 µm, and >10.0 µm. Air is sampled at 28.3 L/min (1.0 ft3/min) through the particle sizing section 220 and all of the aerosol processed through the 9510 counter goes to the concentration 230. The concentrator minor (lower) flow 232 (containing most particles) is 1 L/min and fed to the functional components of a 3317 particle fluorescence/viability detector 240 (manufactured by TSI, Inc. of Shoreview, Minn.). A major (higher) flow 234 from concentrator 230 (with a flow rate of about 27.3 to about 26.3 L/min) goes to a blower inlet (not shown) and is exhausted. Minor flow 232 flows through detector 240 and can be controlled by a separate pump or by correct use of control orifices in the major and/or minor flow can be induced by the same blower. As a separate flow item, the aerosol flow through detector 240 is surrounded by 4 L/min of filtered, clean "sheath air" to confine the particle path, maintain particles at a uniform velocity, and prevent contamination of the optics.

Figure 6:
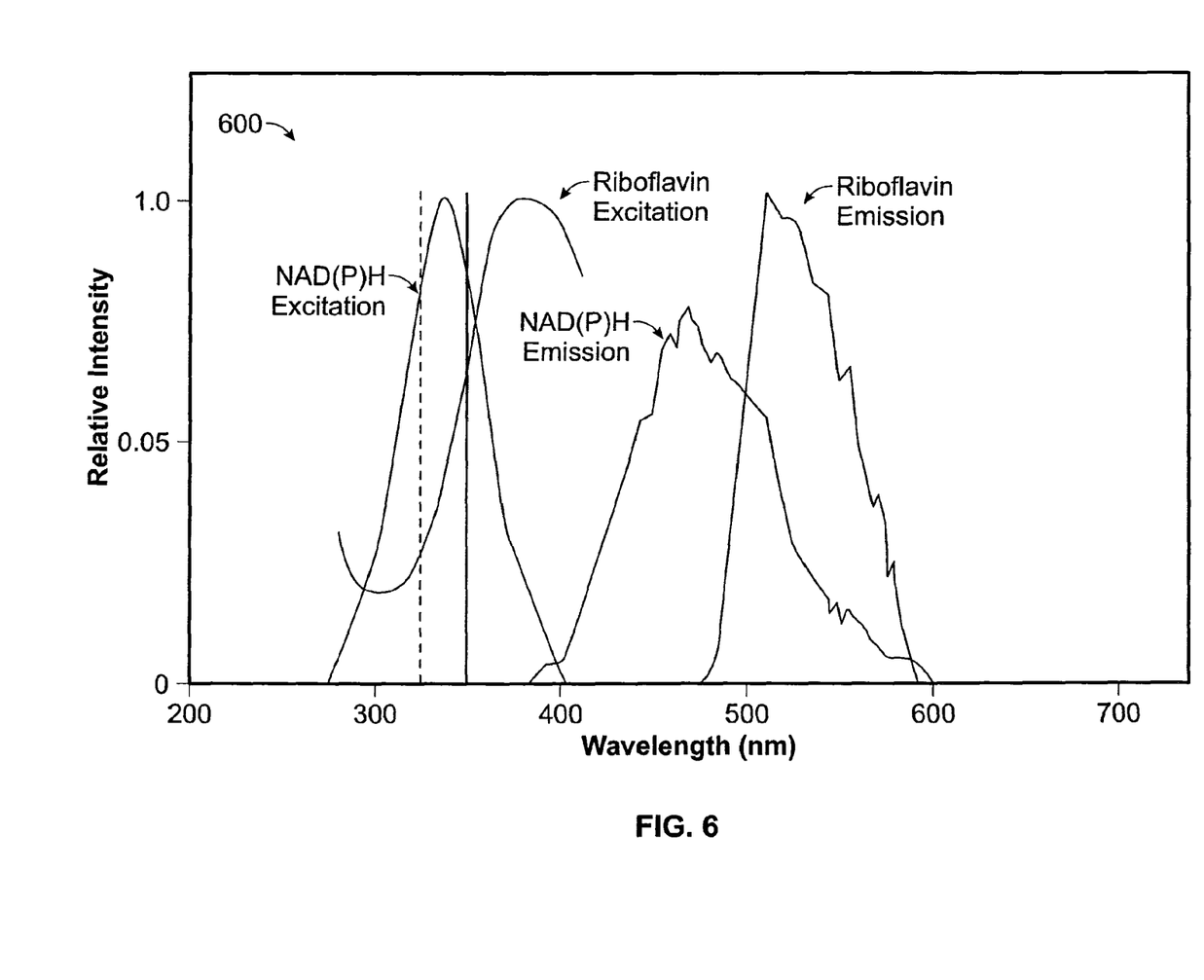
FIG. 6 illustrates a graph of various curves illustrating fluorescence excitation and emission data for various constituents of microbial particles.

In the various embodiments described herein, viable particle detection is based on the use of TSI's Model 3317 Fluorescence Aerosol Particle Sensor (FLAPS III). In one example embodiment, viability determination is made by measuring intrinsic fluorescence of the individual particles excited by a 405 nm diode laser, with emissions measured in two wavelength bands: 430 to 500 nm (referred to as fluorescence channel 1, or FL1), and 500 to 600 nm (referred to as fluorescence channel 2, or FL2), and scattered 405 nm light (referred to as LS). The measured fluorescence is indicative of microbial fluorophores, including NAD(P)H and riboflavin, for which fluorescence curves are illustrated in FIG. 6. This type of approach helps with differentiation or discrimination between viable and non-viable particles. Particle light scatter is also measured by the viability detector and provides a second measurement of particle size. The fluorescence emissions and light scatter signal at predetermined intensities and ratios of intensities among the 3 measurements give a useful indication of a biological particle, and in particular a viable bacterial particle.

It has been observed that the intrinsic fluorescence signal intensities of most biological particles are much weaker (typically by a factor greater than 100) than the scattered light signals, which makes the direct viability detection in 28.3 L/min or higher of aerosol flow not feasible with excitation sources that have practical size, weight, and cost. To compensate for this, the various particle detection systems described herein include a particle concentrator which directs most of the particles in the 28.3 L/min outlet flow from the particle sizer into the 1 L/min sample inlet flow of the viability detector. Particle concentrators of this type use a "virtual impactor" inertial method that is widely used to enrich the concentration of micrometer sized particles into an instrument (see U.S. Pat. No. 4,301,002). Concentrators of this type are characterized by an efficiency curve (such as illustrated in FIG. 3) that describes their effectiveness at enriching the particle concentration in the outlet flow as a function of particle size. Referring now to FIG. 3, there is shown an efficiency curve 300 illustrating particle transmission in an inertial aerosol concentrator. The key features of the efficiency curve are the 50% lower cut point (the smallest particle size at which 50% of particles entering the system are delivered to the outlet flow), and the mid-range efficiency (the percentage of particles in the inlet delivered to the outlet in the particle size range well above the cut point). Large particles, approximately 10 µm and above, are measured with lower efficiency by most instruments due to both their tendencies to settle and to impact on surfaces. Since particles delivered to the viability detector pass through both the particle sizer and the concentrator, the overall efficiency of particle transport through the particle sizer and the concentrator characterizes the aerosol that is delivery to the viability detector. In this example embodiment, a 50% efficiency is about 1.5 to 2.5 µm, and a mid-range efficiency is about 70-75%.

The concentrator efficiency curve of FIG. 3, in this example embodiment, will support accurate reporting of viable particles per cubic meter of air by determining the effective flow rate for viability detector 140. For example, 28.3 L/min*0.72 efficiency results in an effective flow of 20.4 L/min. The expected 50% efficiency size is well suited for viable particle detection, because nearly all particles that produce viable colonies are comprised of bacterial clusters or mixtures of bacteria and supporting materials that results in sizes larger than 2 µm. Conversely, few individual bacteria, which are typically in the 0.7 to 2.0 µm size range, remain viable after suspension in air due to dehydration and exposure to light.

Figure 4:
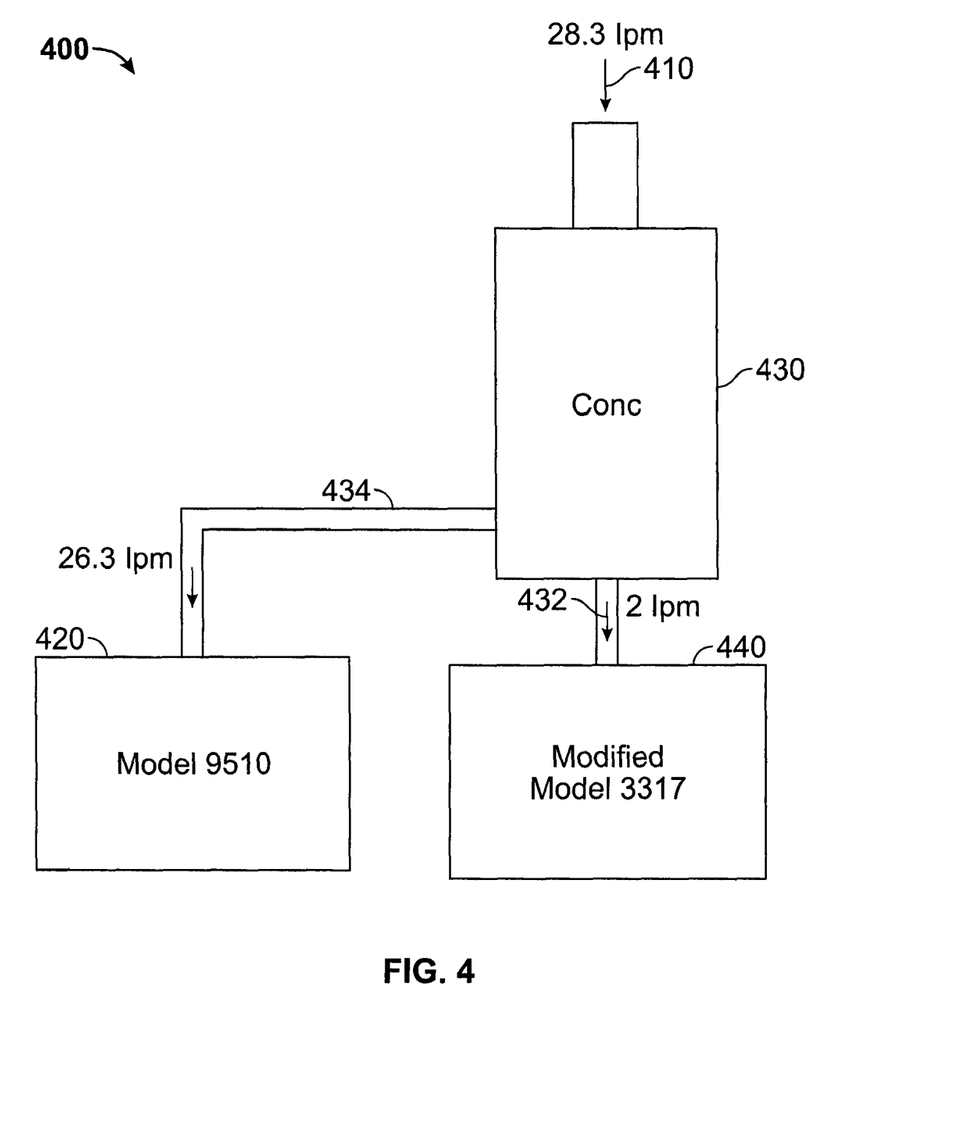
FIG. 4 depicts another embodiment of a particle characterization system detecting substantially simultaneously from an aerosol sample at a high flow rate for both large and small viable and nonviable particles.

Referring now to FIG. 4, in a related embodiment, a system 400 and method for novelly achieving particle characterization with particle sizing and fluorescence sensing at a relatively high flow rate, (e.g., 28.3 L/min) is described. Generally, the use of a particle concentrator at an inlet (such as inlet 410) to fluorescence instruments is widely done, so the inspection time for each particle is increased relative to what that time would be in the unconcentrated aerosol flow, which thereby improves the signal to noise ratio of the fluorescence (and light scatter) measurements. However, if a separate, higher flow particle sizer instrument were to be used simply in parallel with a biological particle characterization instrument with a concentrator inlet, the result would be ambiguity between the two measurements since the sampled aerosol volume would be different for the two methods. For example, it would be possible to sense a larger number of biological particles than of total particles. In this example method, an aerosol sample flowing at about 28.3 liters per minute is first sampled by an aerosol concentrator 430 at inlet 410. Concentrator 430 has two aerosol output ports: a lower "minor" flow 432 (at about 2 liters per minute), which contains most of the larger particles falling to the right of an efficiency curve as illustrated in FIG. 3, and a higher "major" flow 434, which contains most of the smaller particles falling to the left of an efficiency curve as illustrated in FIG. 3. Minor flow 432 is then fed to a fluorescence instrument 440 with optical sizing capability (labeled "Modified 3317"), while major flow 434 is fed to an optical particle sizing instrument 420 capable of detecting smaller particles (labeled "9510"). In this way, the particles entering system 400 at inlet 410 are all sampled, with the overall size distribution being the sum of particles measured from the minor and major flow, and the viable biological particles are measured in the minor flow, as in the embodiment described above. In this example embodiment, a collection filter is added at the outlet of device 440.

The various embodiments described herein can be used in other applications such as particle sensors in "clean environments," to identify sources of particle intrusions, both for non-specific particles and for biological particles. This is typically done by moving the inlet of a particle instrument, either by physically moving the instrument or by moving the inlet of a sampling hose connected to the instrument inlet, in such a way as to detect an increase in particle measurements at or near the location of an intrusion.

Another feature of the viable particle discrimination technique embodied in the invention is the capability to change the size and position, within the 3-dimensional parameter space of FL1, FL2, and LS, of the "target region" which identifies particles a viable. This provides the ability to count predominately some viable particle types, such as bacterial spores, while not counting other viable particle types, such as fungi. Alternatively or additionally, this allows the response of the instrument to be selected more or less sensitive to particles with fluorescence and light scatter signals similar to viable particles. Viable particles have inherent variability due to growth conditions, life cycle stages, inclusion of inert components, and other factors. Similarly, nonviable particles have significant variability due to possible inclusion of inert fluorescent materials or biological fragments. Consequently, the possibility exists for both false positive classification of a non-viable particle as viable, and false negative classification of a viable particle as non-viable. Controlled adjustment of the size and/or location of the target region provides for selection of the trade-off between false positives and false negatives suited to the application and conditions being measured. For example, in monitoring an area where a high degree of cleanliness is important, it is important to minimize false negatives, so a high sensitivity setting is desirable. Alternatively, for an area with a relatively high number of inert particles for which only a moderate level biological cleanliness is needed, a lower sensitivity setting may be desired to provide a low false positive rate while still detecting any significant increase in biological particles. In the preferred embodiment, two sensitivity selections are provided, which the selection protected by a password to prevent unauthorized changes to the setting. In addition, the sensitivity setting is archived with the data output.

Figure 5:
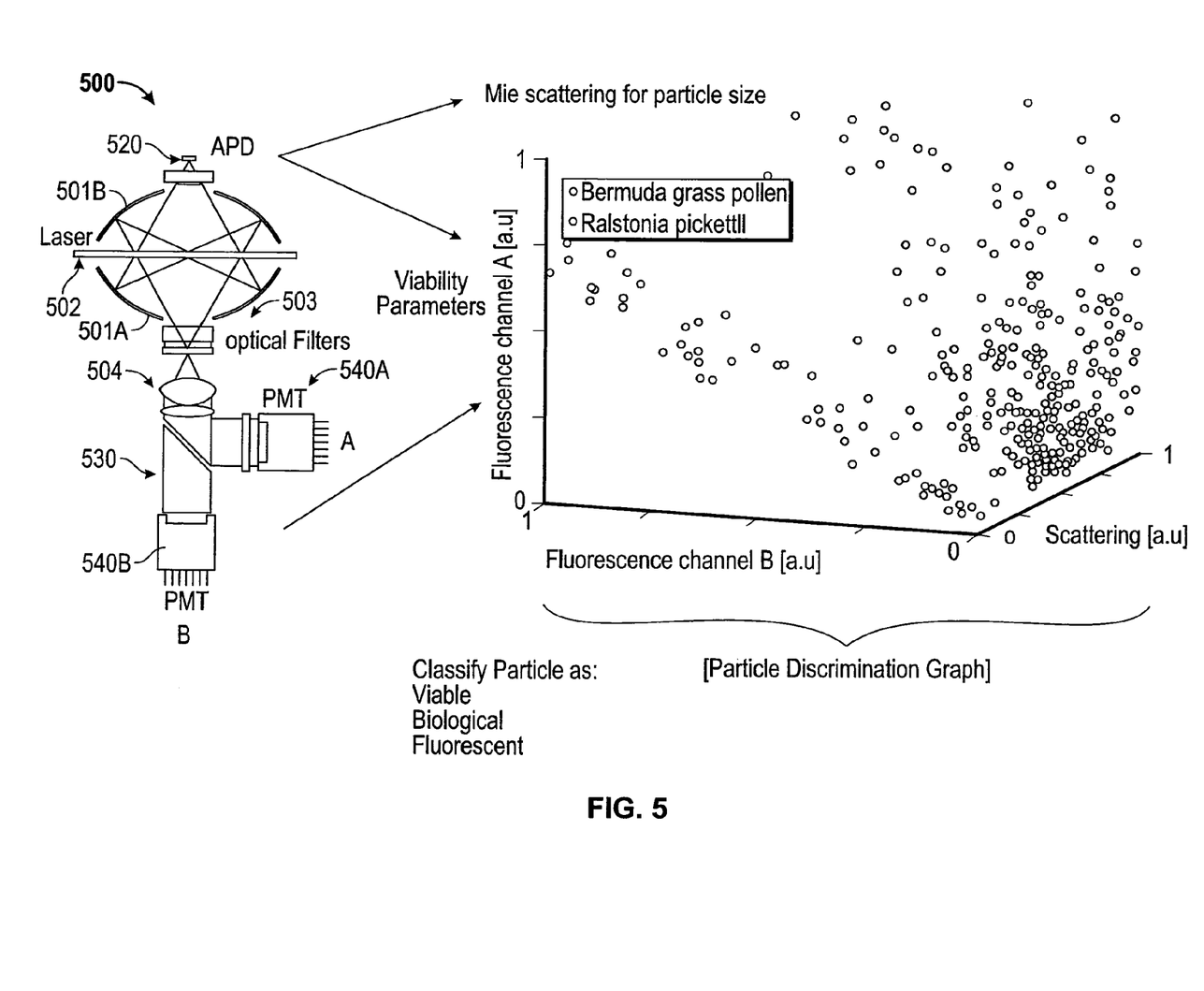
FIG. 5 depicts a particle viability subsystem associated with the various embodiments disclosed herein illustrating particle discrimination capabilities according to the teachings of the invention.

Referring now to FIG. 5, there is shown a viability detector subsystem 500 of a particle characterization system illustrated schematically as detector 140 or detector 240. In subsystem 500, the particles from a minor flow output of an aerosol concentrator flow through the center of the region defined by a pair of ellipsoidal mirrors (501A (lower) 501B (upper)), with the flow perpendicular to both a laser source (502) and to the axis of detector, 520, 540A, and 540B. Scattered light is reflected by ellipsoidal mirror 501A and directed onto an avalanche photodetector (APD) 520, while essentially simultaneously scattered light and fluorescence emissions from a particle are reflected by ellipsoidal mirror 501B onto optical filter(s) 503 that block scattered light and any background light at the excitation wavelength. The remaining fluorescence light is approximately collimated by the lenses 504 and directed to a dichroic filter 530 which separates the fluorescence light into two wavelength bands, with the shorter wavelength band directed at photomultiplier tube (PMT) 540A (on the upper right), and the longer wavelength band directed at photomultiplier tube (PMT) 540B (lower left on the page). The signals from each of the three detectors are conditioned, digitized, and communicated to electronic and software data processing that discriminate measured parameters for viable particles from those of nonviable particles. The discrimination capability is illustrated in the accompanying graph which show measurements of two particle types, *Ralstonia pickettii*, a bacterial target for detection, and Bermuda grass pollen, a nonviable, potential interferent particle in clean areas. The graph shows clear separation between the two particle types in the 3 dimensional space defined by the measured parameter.

In other related embodiments of the characterization systems, methods other than fluorescence that are enhanced by aerosol concentration could alternatively, or in combination, be used, such as Laser Induced Breakdown Spectroscopy, Spark Induced Breakdown Spectroscopy, Raman spectroscopy, Infrared Absorption spectroscopy, and mass spectroscopy.

In the various embodiments described herein, the concentrator type used herein is described in U.S. Pat. No. 7,261,007 and is incorporated herein by reference in its entirely.

In other related embodiments, various optical particle counting systems described herein have general use for any application where it is desired to both (a) measure all particles at a higher flow rate and (b) screen for other particles having an optical property (such as fluorescence or LIBS/S IBS spectral features) that is preferably measured at a lower flow rate. Other applications using the particle counting systems described herein include, but are not limited to, monitoring for particles with a toxic or allergenic property; process control applications where it is desirable to measure the ratio of particles having a given optical property to those without; hospital controlled areas such as surgery suites, controlled rooms (infectious patients or immune compromised), pharmacies and drug or sensitive material compounding areas.

The following patents or publications that relate to OPC devices are herein incorporated by reference in their entirety and constitute part of the disclosure herein: U.S. Pat. Nos. 5,118,959; 5,701,012; 5,895,922; 6,831,279; 7,407,531; and 7,261,007.

Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

We claim:

1. A particle characterization system comprising:
an optical particle counter or sizer with an inlet configured to receive an aerosol particle sample directly from a monitored area at a particle counter inlet flow rate sufficient to sample one cubic meter of the aerosol particle sample in less than an hour, the optical particle counter adapted to use light scattering to measure the particles in the aerosol sample at least as small as about 0.5 micrometers with at least about 50% efficiency;
an aerosol particle concentrator having a concentrator inlet of which is coupled to an outlet of the optical particle counter or sizer and adapted to receive the aerosol particle sample from the monitored area at the particle counter inlet flow rate from the optical particle counter or sizer and configured to emit a major flow at a major flow rate and emit a portion of the aerosol particle sample with an enriched concentration of particles therein at a minor flow rate that is lower than the particle counter inlet flow rate, wherein the concentrator includes a first and a second annular housing section with cooperating annular nozzle sections that form an annular acceleration nozzle, the concentrator including an exit aperture and a conduit attached to the second annular housing section; and
an optical spectral measurement device coupled to a concentrator outlet of the concentrator and configured to receive the enriched aerosol particle sample at the lower minor flow rate and is measured at a rate equivalent to least about one cubic meter per hour, the spectral measurement device adapted to spectrally measure light emitted or absorbed by the particles in the enriched aerosol sample and thereby discriminate intrinsic fluorescence of biological particles at least as small as about 2.0 micrometers with at least about 50% efficiency,
wherein the system is configured in a single instrument to measure a total particle count and sort in a size distribution the particles in the aerosol sample directly from the monitored area and measure biological particle count in the aerosol particle sample from the monitored area at the particle counter inlet flow rate, and wherein the system is configured to receive the aerosol particle sample at the particle counter inlet flow rate without using a second concentrator or virtual impactor.

2. The particle characterization system of claim 1, wherein the spectral measurement is used to determine one or more constituents of the particle.

3. The particle characterization system of claim 2 in which 2 or more settings are provided to alter the sensitivity of the determination of the particle constituent.

4. The particle characterization system of claim 2, wherein the spectral measurement is used to determine if the particles include biological constituents.

5. The particle characterization system of claim 1, wherein the spectral measurement is fluorescence.

6. The particle characterization system of claim 5, wherein the fluorescence measurement is used to determine if the particles include biological constituents.

7. The particle characterization system of claim 2, wherein the spectral measurement is selected from the group consisting of Laser Induced Breakdown Spectroscopy, Spark Induced Breakdown Spectroscopy, Raman spectroscopy, Infrared Absorption spectroscopy, and mass spectroscopy.

8. The particle characterization system of claim 1, further comprising an electronic and software data processor that discriminates measured parameters for biological or viable particles from those of non-biological or nonviable particles.

9. The particle characterization system of claim 1, wherein the minor flow rate is about 10% of the particle counter inlet flow rate.

10. The particle characterization system of claim 1, wherein the particle counter inlet flow rate is about 28.3 to about 30.3 liters per minute and the minor flow rate is about 0.5 to about 4 liters per minute.

11. The particle characterization system of claim 1, further comprising a collection filter operatively coupled to the outlet of the spectral measurement device and adapted to collect particles from the spectral measurement device to provide for a secondary, off-line assessment of particle viability or composition.

12. A particle characterization system comprising:
an aerosol particle concentrator having an inlet configured to receive an aerosol particle sample flow from a monitored area at a concentrator inlet flow rate sufficient to sample one cubic meter of the aerosol sample in less than an hour, the concentrator configured to emit a majority of the sample flow at a lower major flow rate, and emit a minority of the sample flow containing an enriched concentration of the aerosol particles at a minor flow rate that is lower than each of the concentrator inlet and major flow rates, wherein the concentrator includes a first and a second annular housing section with cooperating annular nozzle sections that form an annular acceleration nozzle, the concentrator including an exit aperture and a conduit attached to the second annular housing section;
an optical particle counter or sizer having an inlet of which is coupled to an outlet of the concentrator emitting the major flow, the optical particle counter or sizer adapted to use light scattering to count the particles in the major flow sample at least as small as about 0.5 micrometers with at least about 50% efficiency; and
a spectral measurement device having a spectral measurement inlet coupled to a concentrator outlet of the concentrator emitting the minor flow, the spectral measurement device configured to receive the enriched aerosol sample flow, measured at a rate equivalent to least about one cubic meter per hour, and adapted to spectrally measure light emitted or absorbed by the particles in the enriched aerosol sample to thereby discriminate intrinsic fluorescence of biological particles at least as small as about 2.0 micrometers with at least about 50% efficiency,
wherein the system is configured in a single instrument to measure at a sample flow rate of at least one cubic foot per hour a total particle count as the sum of particles measured in the major flow and minor flow, and to sort in a size distribution the particles in the aerosol sample directly from the monitored area, and to measure biological particle count in the aerosol sample from the monitored area at the concentrator flow rate.

13. The particle characterization system of claim 12, wherein the spectral measurement is used to determine one or more constituents of the particles.

14. The particle characterization system of claim 13, wherein the spectral measurement is used to determine if the particles include biological constituents.

15. The particle characterization system of claim 12, wherein the spectral measurement is fluorescence and the fluorescence measurement is used to determine if the particles include biological constituents.

16. The particle characterization system of claim 13, wherein the spectral measurement is selected from the group consisting of Laser Induced Breakdown Spectroscopy, Spark Induced Breakdown Spectroscopy, Raman spectroscopy, Infrared Absorption spectroscopy, and mass spectroscopy.

17. The particle characterization system of claim 12, further comprising an electronic and software data processer that discriminates measured parameters for biological or viable particles from those of non-biological or nonviable particles.

18. The particle characterization system of claim 12, wherein the minor flow rate is about 10% of the concentrator inlet flow rate.

19. The particle characterization system of claim 18, wherein the concentrator inlet flow rate is about 28.3 to about 30.3 liters per minute and the minor flow rate is about 1 to about 4 liters per minute, with the concentrator major outlet flow rate being the difference between the concentrator inlet flow and concentrator minor outlet flow.

20. The particle characterization system of claim 12, further comprising a collection filter operatively coupled to an outlet of the spectral measurement device and adapted to collect particles from the spectral measurement device to provide for a secondary, off-line assessment of particle viability or composition.

21. A method of counting particles and of characterizing the viability of the particles in an aerosol sample that is flowing at a high rate, the method comprising the steps of:
receiving the aerosol sample at an optical particle counter or sizer with an inlet from a monitored area at a particle counter inlet flow rate sufficient to sample one cubic meter of the aerosol sample in less than an hour and using light scattering to measure or count the particles in the aerosol sample at least as small as about 0.5 micrometers with at least about 50% efficiency;
configuring with an aerosol particle concentrator a portion of the aerosol sample that is at the particle counter inlet flow rate to have an enriched increased concentration of particles therein and to flow at a minor flow rate, wherein then minor flow rate is lower than the particle counter inlet flow rate and is sufficiently low to spectrally measure light emitted by the particles;

spectrally measuring light emitted or absorbed by the particles in the particle enriched aerosol sample received from an outlet of the concentrator, measured at a rate equivalent to least about one cubic meter per hour and thereby discriminate intrinsic fluorescence of biological particles at least as small as about 2.0 micrometers with at least about 50% efficiency, and providing both a total particle count measurement, sorting in a size distribution the particles in the aerosol sample, and providing a measurement of biological particle count in the aerosol sample from a single instrument using the aerosol sample from the monitored area at the particle counter inlet flow rate.

22. The method of claim 21, wherein the particle enriched aerosol sample is configured using the concentrator that is coupled to the optical particle counter that receives the aerosol sample at the particle counter inlet flow rate, wherein the concentrator includes a first and a second annular housing section with cooperating annular nozzle sections that form an annular acceleration nozzle, the concentrator including an exit aperture and a conduit attached to the second annular housing section from which the particle enriched aerosol sample flows from the concentrator at the minor and lower rate.

23. A method of counting particles and characterizing the viability of the particles in an aerosol sample that is flowing at a high rate, the method comprising the steps of:

configuring with an aerosol particle concentrator with an inlet a portion of the aerosol sample that is received from a monitored area at a concentrator inlet flow rate sufficient to sample one cubic meter of the aerosol sample in less than an hour to have an enriched increased concentration of particles therein, emitting from a first outlet of the concentrator a majority of the received sample flow at a major flow rate that is lower than the concentrator inlet flow rate, and emitting from a second outlet of the concentrator a minority of the sample flow containing an enriched concentration of the aerosol particles at a minor flow rate that is lower than each of the concentrator inlet and major flow rates;

providing an optical particle counter or sizer that receives from the first outlet of the concentrator the majority of the aerosol sample at the major flow rate and uses light scattering to count the particles in the majority aerosol sample at least as small as about 0.5 micrometers with at least about 50% efficiency; and providing a spectral measurement device that receives from the second outlet of the concentrator the minority aerosol sample flow at the minor flow rate, measured at a rate equivalent to least about one cubic meter per hour to thereby discriminate intrinsic fluorescence of biological particles at least as small as about 2.0 micrometers with at least about 50% efficiency and spectrally measures the light emitted or absorbed by the particles in the aerosol sample; and providing a total particle count measurement, sorting in a size distribution the particles in the aerosol sample and providing a measurement of biological particle count in the aerosol sample from a single system using the aerosol sample from the monitored area at the concentrator inlet flow rate.

24. A particle characterization system comprising:

an optical particle counter or sizer with an inlet configured to receive an aerosol particle sample directly from a monitored area at a particle counter inlet flow rate sufficient to sample one cubic meter of the aerosol sample in less than an hour, the optical particle counter adapted to use light scattering to measure the particles in the aerosol sample at least as small as about 0.5 micrometers with at least about 50% efficiency;

an aerosol particle concentrator having a concentrator the inlet of which is coupled to an outlet of the optical particle counter or sizer and adapted to receive the aerosol sample at the particle counter inlet flow rate from the optical particle counter or sizer and configured to emit a major flow at a major flow rate and emit a portion of the aerosol sample with an enriched concentration of particles therein at a minor flow rate that is lower than the particle counter inlet flow rate; and an optical spectral measurement device coupled to an outlet of the concentrator and configured to measure at a rate equivalent to at least one cubic meter per hour and receive the enriched aerosol sample at the lower minor flow rate, the spectral measurement device adapted to spectrally measure light emitted or absorbed by the particles in the enriched aerosol sample to thereby discriminate intrinsic fluorescence of biological particles at least as small as about 2.0 micrometers with at least about 50% efficiency, wherein the system is configured in a single instrument to measure a total particle count and sort in a size distribution the particles in the aerosol sample directly from the monitored area and measure biological particle count in the aerosol sample from the monitored area at the particle counter inlet flow rate, and wherein the system is configured to receive the aerosol sample at the particle counter inlet flow rate without using a second concentrator or virtual impactor.

25. The method of claim 21 further comprising the step of combining a first set of particle measurement data at the major flow rate and a second set of particle measurement data from the spectral measurement device at the minor flow rate to generate the total particle measurement or count for the aerosol sample at the particle counter inlet flow rate.

26. The method of claim 23 further comprising the step of combining a first set of particle measurement data from the optical particle counter or sizer at the major flow rate and a second set of particle measurement data from the spectral measurement device at the minor flow rate to generate the total particle measurement or count for the aerosol sample at the concentrator inlet flow rate.

27. The system of claim 24 further comprising a sheath air flow surrounding the sampled aerosol within the spectral measurement device.

* * * * *